United States Patent
Homestad

(10) Patent No.: US 7,754,918 B1
(45) Date of Patent: Jul. 13, 2010

(54) CRYSTALLIZATION OF IODIXANOL IN ISOPROPANOL AND METHANOL

(75) Inventor: Ole Magne Homestad, Spangereid (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 12/613,730

(22) Filed: Nov. 6, 2009

Related U.S. Application Data

(60) Provisional application No. 61/227,104, filed on Jul. 21, 2009.

(51) Int. Cl.
*C07C 233/64* (2006.01)
(52) U.S. Cl. ..................................... 564/153
(58) Field of Classification Search ........................ None
See application file for complete search history.

(56) References Cited

U.S. PATENT DOCUMENTS 6,646,171 B2    11/2003  Cervenka

2008/0214867 A1    9/2008  Cervenka et al.
2008/0287711 A1 *  11/2008  Strandmyr ................. 564/153
2009/0253935 A1 *  10/2009  Cervenka et al. ........... 564/153

OTHER PUBLICATIONS

Database CAS citation 1999:249107 [retrieved Dec. 14, 2009] from STN; Columbus, OH, USA.*
Database CAS citation 2007:113970 [retrieved Dec. 14, 2009] from STN; Columbus, OH, USA.*

* cited by examiner

*Primary Examiner*—Karl J Puttlitz

(57) ABSTRACT

A process for the manufacture of iodixanol by performing a crystallization process of the crude product in a solvent mixture comprising water, methanol and isopropanol. The crude product may be obtained in aqueous solution from dimerisation of 5-acetamido-N,N'-bis(2,3-dihydroxypropyl)-2,4,6-triiodo-isophthalamide ("Compound A").

1 Claim, No Drawings

CRYSTALLIZATION OF IODIXANOL IN ISOPROPANOL AND METHANOL

CROSS REFERENCE TO RELATED APPLICATIONS

The present application claims benefit of priority under 35 U.S.C. §119(e) to U.S. Provisional Application No. 61/227,104 filed Jul. 21, 2009, the entire disclosure of which is hereby incorporated by reference.

FIELD OF THE INVENTION

This invention relates to the manufacture of iodixanol (1,3-bis(acetamido)-N,N'-bis[3,5-bis(2,3-dihydroxypropylaminocarbonyl)-2,4,6-triiodophenyl]-2-hydroxypropane).

BACKGROUND

Iodixanol is the non-proprietary name of the chemical drug substance of a non-ionic X-ray contrast agent marketed under the trade name Visipaque™. Visipaque™ is one of the most used agents in diagnostic X-ray procedures and is manufactured in large quantities.

The manufacture of such non-ionic X-ray contrast agents involves the production of the chemical drug substance (referred to as primary production) followed by formulation into the drug product (referred to as secondary production). Primary production of iodixanol involves a multi step chemical synthesis and a thorough purification process. For a commercial drug product it is important for the primary production to be efficient and economical and to provide a drug substance fulfilling the specifications, e.g. as expressed on the US Pharmacopeia.

A number of methods are known for the preparation of iodixanol. These are all multi step chemical synthetic processes and the cost of the final formulated product thus mainly depends on these processes. It is therefore important to optimize the processes both for economic and environmental reasons.

Three main chemical synthetic processes are known for the preparation of iodixanol, all of which start with 5-nitroisophthalic acid. In the first process described in EP patent 108638, which document is hereby incorporated by reference, the final intermediate 5-acetamido-N,N'-bis(2,3-dihydroxypropyl)-2,4,6-triiodo-isophthalamide (hereinafter "Compound A") is reacted with a dimerisation agent such as epichlorohydrin to yield the drug substance, see Scheme I.

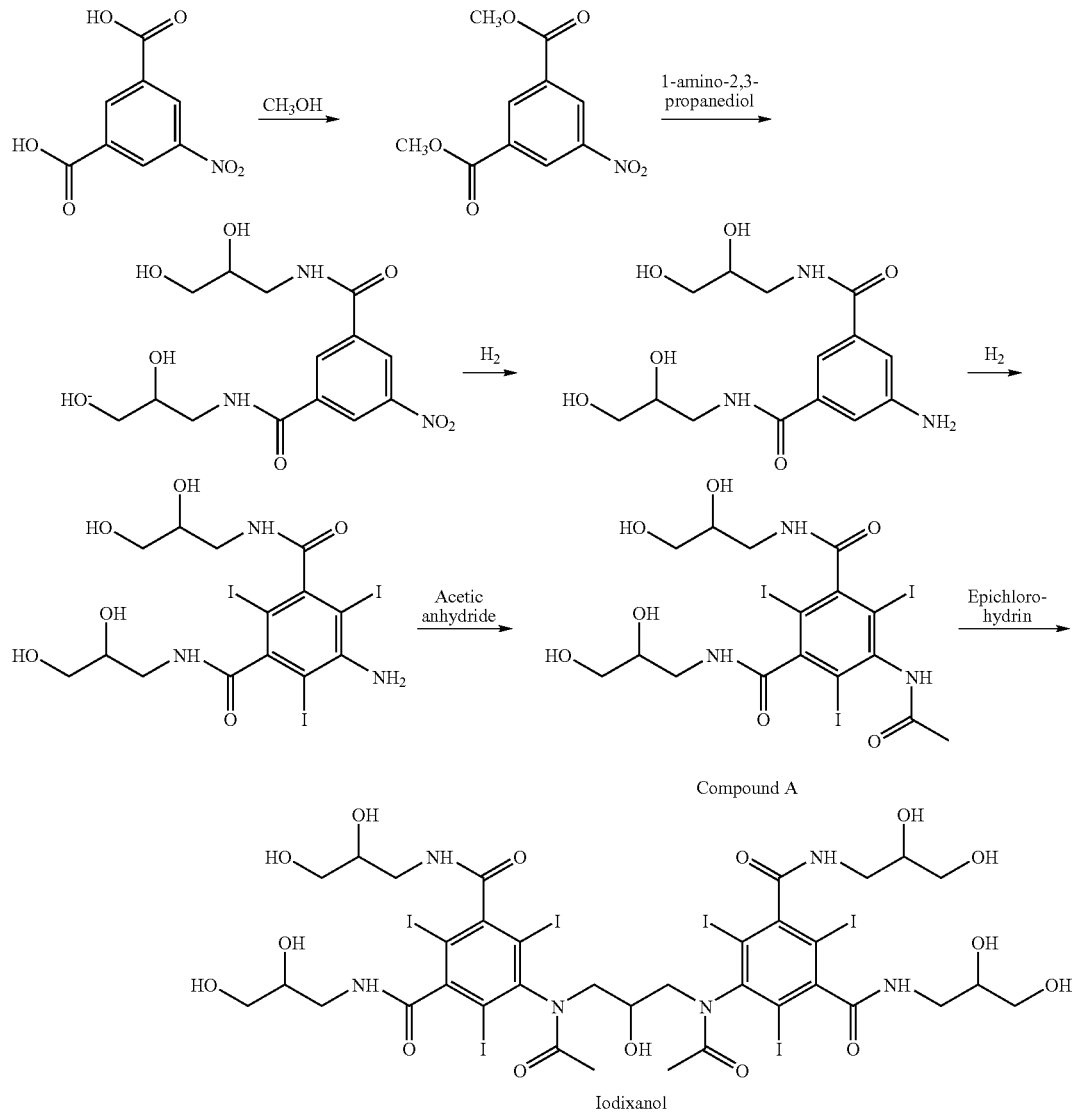

Scheme I

The overall yield in this process is relatively low and the purification of the end product iodixanol is expensive and time consuming. The purification process described in EP patent 108638 involves purification by preparative liquid chromatography. The use of preparative liquid chromatography is a serious disadvantage in industrial processes in particular due to the high costs involved.

Several attempts have been made to find alternative manufacturing processes. Attempts to increase the yield of the chemical synthesis is published by Priebe et. al. (Acta Radiol. 36 (1995), Suppl. 399, 21-31). This publication describes another route which avoids the difficult last step of the process of Scheme I. However, the route involves eight reaction steps from 5-nitroisophthalic acid, which is undesirable, and one of the steps includes chlorination with thionyl chloride, which is extremely corrosive. Also, the introduction of the iodine atoms takes place very early in the sequence, which is disadvantageous as iodine is the most expensive reagent in the process. The yield and final purification method for this route have not been reported.

The third route to iodixanol involves the synthesis of 5-amino-2,4,6-triiodoisophthalic acid (WO 96/37458) and then its dichloride (WO 96/37459), followed by conversion into Compound A (U.S. Pat. No. 5,705,692) and finally dimerisation as in the process of Scheme I. This method thus has the same disadvantages as the first process, and also uses an undesirable acid chlorination step.

Several attempts have also been made to find alternative purification procedures avoiding the liquid chromatography method described in European patent 108636.

WO 99/18054 describes a process for the crystallization of i.a. iodixanol where the crystallization is effected with high thermal energy, specifically under elevated pressure and at a temperature above the boiling point of the solution at atmospheric pressure. A number of suitable solvents are listed at page 3 of the document, including $C_{1-4}$ alcohols such as methanol and isopropanol (propan-2-ol, 2-propanol). A mixture of methanol and propan-2-ol is noted as the preferred solvent according to this invention.

WO 2007/013815 describes a continuous crystallization process of iodixanol where using a solvent mixture comprising methanol/water/2-propanol is described.

WO 2006/016815 describes a process for the crystallization of iodixanol with 1-methoxy-2-propanol as solvent.

WO 2007/064220 describes a process for the crystallization of iodixanol with ethanol as solvent.

WO 2007/073202 describes a process for the crystallization of iodixanol with n-propanol as solvent.

It is hence a desire to identify a purification process wherein crude iodixanol as obtained by N-alkylation of Compound A as illustrated in Scheme I, and hereinafter denoted "dimerisation", can be obtained in a sufficiently pure form preferably by one single crystallization step. The requirements to such process are: The total crystallization time should be shortened and should not exceed 4 days. It is further desirable to achieve a more cost-efficient purification process by reducing the energy input and reducing the amounts of solvents needed in the process, in addition to achieve a higher output of product per unit reactor volume.

The purity of the crude iodixanol is typically only 83-84%, which means that the purification effect in the crystallisation needs to be very good to yield a product within the quality requirements. At the same time iodixanol is produced in large quantities, so the yield in the process is very important in terms of financial performance.

The crude iodixanol from the preceeding process step is dissolved in water before the crystallisation step. This is a challenge, since even small amounts of water in the mother liquor of the crystallisation increases the solubility of iodixanol significantly. We have now surprisingly found that minimization of the water content in the mother liquor combined with gradual addition of isopropanol during the crystallisation overcomes this problem.

Hence, it has now surprisingly been found that using a solvent mixture comprising water, methanol and isopropanol in the purification step of crude iodixanol will fulfill one or more of the requirements listed above.

SUMMARY OF THE INVENTION

The present invention provides a process for the purification of a crude product containing about 75-90 weight % iodixanol, 3-10 weight % iohexyl, 0-7 weight % Compound A and minor amounts of other impurities by crystallization comprising the steps of
 a) adjusting the water content in an aqueous solution of the crude product to reach the desired water concentration;
 b) adding about 1 to 3 l methanol per kg iodixanol;
 c) gradually adding a total of about 1.5 to 4 l isopropanol per kg iodixanol in one or several portions.

DETAILED DESCRIPTION OF THE INVENTION

Further embodiments of the invention are specified in the attached claims.

Crude product is obtained from the processes known from the state of art, e.g. from the dimerisation process illustrated in Scheme I above. The dimerisation step itself may be carried out as described in European patent 108638 and WO 98/23296, for example using epichlorohydrin as the dimerisation agent. The reaction is usually carried out in a non-aqueous solvent such as 2-methoxyethanol, and generally results in the conversion of 40 to 60% of Compound A to iodixanol. Preferably, unreacted Compound A is precipitated from the reaction mixture and recovered for reuse in a later batch as described in WO 00/47549.

The crude product from the dimerisation and following work-up steps is in aqueous solution with small traces of organic solvent. The crude product contains about 75-90 weight % iodixanol, 3-10 weight % iohexyl, 0-7 weight % Compound A, and also minor amounts of other impurities. This crude product is the starting material for the further purification, which comprises crystallization, from a solvent mixture comprising water, methanol and isopropanol. The work-up procedures are those conventionally used and known from the state of the art.

In the crystallization process, the crude product comprising iodixanol in aqueous solution is adjusted to the maximum concentration. The water removal may be performed by distillation or by other evaporation techniques, e.g. falling film or thin film evaporation. Membrane separation techniques, e.g. nanofiltration, may also be used for the purpose of water removal or any combination of the foregoing technologies. After adjusting the water content to the desired level a calculated amount of methanol (initial amount) is added and the mixture is preferably seeded with iodixanol crystals. The solution is preferably kept at elevated temperature, e.g. at reflux, to reduce the supersaturation. Isopropanol is then added in one or preferably several portions, preferably at a slow rate, to increase and maintain the supersaturation as crystal growth occurs. The temperature should be kept at an elevated level, e.g. at reflux, to enhance crystal growth and to maximize the purification effect. Temperatures above the reflux temperature may even be used if an overpressure is applied. Portions of isopropanol may be added after several hours or days of crystal growth.

Methanol is added to the aqueous solution in about 1 to 3 liters per kg iodixanol present, preferably about 2 liters per kg.

Isopropanol is added in a total amount of about 1.5 to 4 liters per kg iodixanol, preferably about 2 liters per kg iodixanol.

Prior to the purification process step the crude product is preferably desalinated, e.g. by nanofiltration removing salt formed during the chemical synthesis, and preferably also reduction of the amount of residual starting material (Compound A) is performed e.g. by ultrafiltration. Any organic solvent used during the chemical synthesis should also be reduced if necessary to an amount not interfering substantially with the purification process.

The solubility of crude product in the solvent mixture of water, methanol and isopropanol is also to some extent dependent on salt content, hence the amount of salts present in the feed should be kept low, preferably below 1.0 w/w % with respect to crude iodixanol. The amount of isopropanol added may be adjusted according to actual levels of water and salts in the mixture.

The precipitate preferably in the form of crystalline product is collected, filtered and washed, preferably with an alkanol such as n-propanol or preferably with methanol. One single purification step will usually be sufficient to obtain iodixanol in a purity satisfying the pharmacopeial specification. The total purification process will take from 1 to 4 days, preferably 1 to 3 days and usually 2 to 3 days is adequate.

The following non-limiting examples illustrate the invention.

EXAMPLES

Example 1

Crude iodixanol (about 700 kg, HPLC purity 83-84%) dissolved in water is concentrated on a falling film evaporator followed by conventional distillation to a viscous solution that contains about 0.17-0.18 L water/kg crude iodixanol. Methanol (1400 L) is added under reflux, and the solution is seeded with crystalline iodixanol (about 2-3 kg). Isopropanol (540 liter) is added at a rate of 50-100 L/hour under reflux. After 30 hours more isopropanol (about 700 L) is added at the same low rate. A third isopropanol addition may be made. At least 65 hours after seeding and when the mother liquor concentration is 7.0 w/v % or lower, the suspension is filtered on a pressure filter at 60° C. and up to 1 bar overpressure of nitrogen. The resulting filter cake is washed with methanol at about 60° C. (totally 750 L). The HPLC purity of the crystals is 98.0-98.5%, and the crystallisation yield 85-90% from crude iodixanol.

All patents, journal articles, publications and other documents discussed and/or cited above are hereby incorporated by reference.

The invention claimed is:

1. Process for the crystallization of crude iodixanol comprising the following sequential steps of:
   a) adjusting the water content of an aqueous solution of crude iodixanol to the maximum concentration of iodixanol;
   b) adding about 1 to 3 liters methanol per kg iodixanol to the product of step a); and
   c) gradually adding a total of about 1.5 to 4 liters isopropanol per kg iodixanol in one or several portions to the product of step b).

* * * * *

UNITED STATES PATENT AND TRADEMARK OFFICE
CERTIFICATE OF CORRECTION

| | | |
|---|---|---|
| PATENT NO. | : 7,754,918 B1 | Page 1 of 1 |
| APPLICATION NO. | : 12/613730 | |
| DATED | : July 13, 2010 | |
| INVENTOR(S) | : Ole Magne Homestad | |

It is certified that error appears in the above-identified patent and that said Letters Patent is hereby corrected as shown below:

Claim 1. Process for the crystallization of crude iodixanol comprising the following sequential steps of:
a) adjusting the water content insert -- in -- of an aqueous solution of crude iodixanol to the maximum concentration of iodixanol, wherein said maximum concentration is 0.17-0.18 liters water/kg crude iodixanol;
b) adding about 1 to 3 liters methanol per kg iodixanol to the product of step a); and
c) gradually adding a total of about 1.5 to 4 liters isopropanol per kg iodixanol in one or several portions to the product of step b).

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

PATENT NO.         : 7,754,918 B1
APPLICATION NO.    : 12/613730
DATED              : July 13, 2010
INVENTOR(S)        : Ole Magne Homestad It is certified that error appears in the above-identified patent and that said Letters Patent is hereby corrected as shown below:

Column 6, lines 25-34, claim 1 should read

Process for the crystallization of crude iodixanol comprising the following sequential steps of:
a) adjusting the water content in of an aqueous solution of crude iodixanol to the maximum concentration of iodixanol, wherein said maximum concentration is 0.17-0.18 liters water/kg crude iodixanol;
b) adding about 1 to 3 liters methanol per kg iodixanol to the product of step a); and
c) gradually adding a total of about 1.5 to 4 liters isopropanol per kg iodixanol in one or several portions to the product of step b).

This certificate supersedes the Certificate of Correction issued October 5, 2010.

Signed and Sealed this

Ninth Day of November, 2010

David J. Kappos
*Director of the United States Patent and Trademark Office*